United States Patent [19]

Forssmann et al.

[11] Patent Number: 4,552,348
[45] Date of Patent: Nov. 12, 1985

[54] COUCH FOR PATIENTS

[75] Inventors: Bernd Forssmann, Friedrichshafen; Hans-Heinrich Gerth, Meersburg; Hendrik Zech, Überlingen; Christian Chaussy, Germering, all of Fed. Rep. of Germany

[73] Assignee: Dornier System GmbH, Friedrichshafen, Fed. Rep. of Germany

[21] Appl. No.: 455,836

[22] Filed: Jan. 5, 1983

[30] Foreign Application Priority Data

Jan. 15, 1982 [DE] Fed. Rep. of Germany ....... 3201021

[51] Int. Cl.⁴ ............................................ A61G 15/00
[52] U.S. Cl. ................................................... 269/324
[58] Field of Search .............................. 269/322–328; 128/71, 72, 84 R; 378/209; 5/437, 433

[56] References Cited

U.S. PATENT DOCUMENTS

| 2,002,349 | 5/1935 | Lundeen | 128/72 |
| 2,267,054 | 12/1941 | Thompson | 128/72 |
| 2,660,495 | 11/1953 | Schwalbe | 128/72 |
| 2,851,320 | 9/1958 | Lorang | 269/325 |
| 3,599,962 | 8/1971 | Henry | 269/322 |
| 3,652,851 | 3/1972 | Zaalberg | 269/322 |
| 4,275,472 | 6/1981 | Erck | 269/328 |

*Primary Examiner*—Robert C. Watson
*Attorney, Agent, or Firm*—Ralf H. Siegemund

[57] ABSTRACT

A couch to securely support and keep in place a completely or partially anesthesized patient in a compression-free and strain-free manner, for instance for contact-less comminution of renal calculi, where the patient by means of strongly mutually inclining and individually adjustable rest surfaces (11, 25, 26) in the shoulder area and at the legs is moved into a back position with a slightly raised upper body and angled legs, with a clear back and rectal area, and with placement of the lower arms next to the head so as to assume a stable hollow-back position.

6 Claims, 3 Drawing Figures

COUCH FOR PATIENTS

BACKGROUND OF THE INVENTION

This invention relates to a couch for reliably reclining a completely or partially anesthesized patient, without compression sites or strains, to be used for instance in the contactless nonevasive comminution of kidney stones or renal calculi by means of acoustic shock waves.

The procedure of comminuting kidney stones, shock waves are generated by igniting an underwater spark gap and are focused by a reflector and guided into the body of the patient where they comminute the calculus (U.S. Pat. No. 3,942,531). To be capable of coupling and decoupling the shock waves in an injury-free manner, the body of the patient is supported in a tub filled with degassed water. The renal calculus is located by X-rays. The patient must be positioned precisely so that the calculus is located exactly at the focus of the spatially stationary shock wave reflector, and the body must be maintained in this position for a substantial period of time. The patient is completely or partially anesthesized during the shock wave treatment.

DESCRIPTION OF THE INVENTION

It is the object of the present invention to provide a couch permitting to so position a completely or partially anesthesized patient within a tub that a specific point of his body—for instance a renal calculus or a kidney stone—can be retained for a substantial period of time in a given spatial location (second focus of an ellipsoid). Compression sites that would block blood circulation must be avoided. Due to the extended time of proneness, such compression sites might cause numbness of body parts. Again, straining of body parts must be avoided during anesthesia. Even very short-term strains, as are incurred for instance in sports, can be painful. This applies even more so to stresses of longer duration.

The present invention is based on the recognition that the human body must be supported only at the shoulder and the legs in order to achieve a reliable positioning. Surprisingly, it was found that an anesthesized slack body will not sag or droop through the "hole" between the shoulder rest and the leg rests, whether in air or in water. This result is achieved by means of an intense corresponding array of shoulder supports, thigh and lower-leg pans. The body is made to assume a kind of double prismatic position. The trunk and the thighs rest in a V-shaped "groove", and the thighs and the lower legs on a "prismatic" guide.

Contrary to possible expectations, the hollow-back position desired for treatment is not obtained by increased support in the hip region, rather surprisingly the shoulder support of the invention together with fixation of the arm next to the head suffices, with all of the back area below the shoulder and as far as the buttocks being freely accessible and unsupported.

The invention offers the following advantages:

it is suitable for all ordinary adult statures, it offers free accessibility to the trunk, especially near the kidneys, the patient is solidly supported in places but without compression points and strap-induced strains, it is suited also for completely anesthesized patients, and it provides for simple changeover for treating the right or left kidney.

Patient couches with the features of the present invention can be implemented in many embodiments. When using a tub, the support surfaces are advantageously secured from above to support posts. Many ways are offered to the designer to carry out the options of the present invention with respect to the securing means and the guidance of the support surfaces.

DESCRIPTION OF THE DRAWINGS

The invention will be further illustrated by reference to the accompanying drawings, in which:

FIG. 1 is a side view in elevation of a couch according to the invention. A crane, not shown, is provided with a fork joint 3 bearing pivotal about the axis 2 and liftable along the axis 2 in the manner indicated by the arrows 2a and 2b. A support beam 1 is supported at its center and is pivoted and locked in position about the axis 4. This beam is 1 secured to the fork joint 3, and terminates in the two hinges or pivots 5 and 6. The two hinges 5 and 6 assume two positions being offset by 180°.

Figure 1:
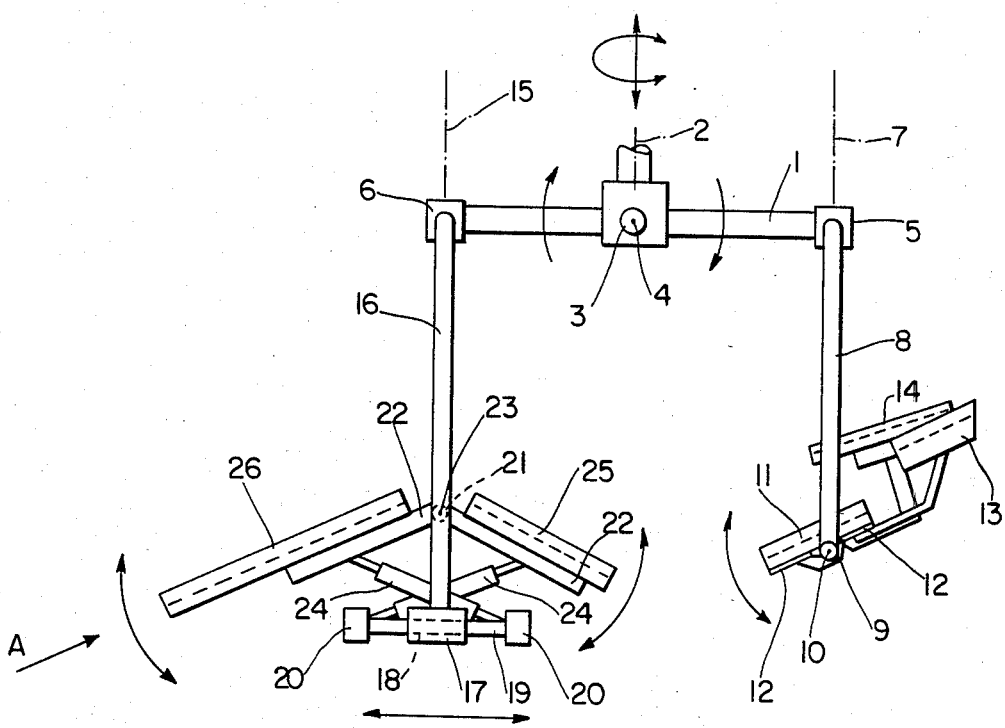
FIG. 1 is a side view of the couch.

A shoulder support 11 being locked in position and rotatable about the axis 10 by means of the articulation 9 is secured to the hinge 5 by an essentially U-shaped support post 8 which is rotatable about the axis 7. The shoulder support 11 is of symmetrical construction and is provided on the underside thereof, to the left and to the right of the axis of rotation 10, in each case with three guides 12. On one side (right in FIG. 1) of these guides, a head rest 13 and two arm rests 14 are so inserted and locked in place that the lower arms lie next to the head (a hands-up position).

A cross-beam 17 containing two parallel, longitudinal guides 18 is secured to the hinge 6 by means of an essentially L-shaped, second support post 16, rotatable about the axis 15. Longitudinally displaceable and locking rails 19 supporting the foot portion of the structure are contained within these guides. The rails 19 are connected by two cross bars 20. The articulations 21 rotatably holding four pan supports 22 pivotal about the axis 23 are located above the rail center. The inclination of the pan support 22 is determined by the length of the spindles 24 arranged cross-wise in each case between a cross bar 20 and the opposite pan support 22. A thigh pan 25 or a lower leg pan 26 is mounted to each pan support 22.

Figure 2:
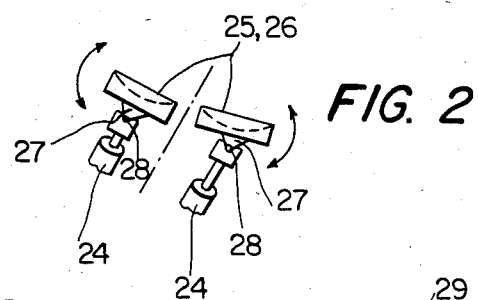
FIG. 2 is a detail from FIG. 1.

FIG. 2 shows two pans 25 or 26 as seen in the A direction (FIG. 1). The pan 26 as well as the pan 25 can be tipped in the articulations 27 about the axis 28 (right-hand partial view) or it can be locked in the neutral position—untipped—(left-hand partial view). The pan shown on the right additionally is raised a slight amount.

Figure 3:
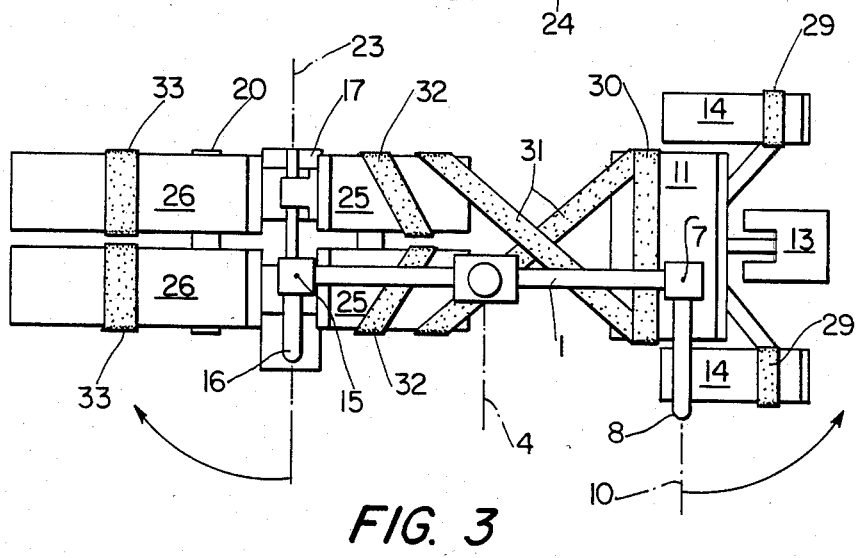
FIG. 3 is a top view of the couch.

FIG. 3 is a top view of the couch of FIG. 1. In addition to the components cited in the description relating to FIG. 1, a strap system, 29 through 33, is shown here. This system is provided to secure the body in place and to counteract the buoyancy in the water-filled tub. The arrangement of the arm rests 14 next to the head results in a hollow-back position of the patient. This position facilitates locating the renal calculus or kidney stone by means of X-ray.

Moreover, the off-center arrangement of the beam 1 with respect to the longitudinal axis of the couch should be noted. This asymmetric suspension serves the purpose of better accessibility of the kidney for location and treatment in the tub. The couch shown in FIGS. 1 and 3 is set up for treating the right kidney. Conversion for treating the left kidney is possible and quickly carried out. The straps 31 are detached, the rest areas 13 for the head, the rests 14 for the arms, and the rests 25 and 26 for the legs are removed, the support post 8 and with it the shoulder support 11 is rotated by 180° about the axis 7 (arrow of FIG. 3), the support post 16 and with it the foot portion is rotated by 180° about the axis 15 (arrow of FIG. 3), and the removed components 13, 14, 25, 26 are plugged in again.

The patient must assume a position slightly to the side for the purpose of locating the kidney calculus and to comminute it. This slight sideways position is achieved by the unilateral raising of one leg pan. Due to the ensuing rotation of the body, all four leg pans 25, 26 will tip, resulting in an advantageous position of the legs. The automatic tipping of the pans prevents compression sites or blood stasis in the anesthesized patient.

Because of its manifold settings (arrows of FIG. 1), the couch can be adjusted precisely to the size and body of the particular patient. This is carried out for instance by a dry run in the unanesthesized state with the corresponding recording of the spindle, joint, and articulation settings so that the optimal settings can be reproduced at the time of treatment. In this manner compression sites are eliminated and no strains result from the straps.

The couch also can be used to anatomically properly place or keep in place those with spinal injuries, or for transverse paralysis.

It will be obvious to those skilled in the art that many modifications may be made within the scope of the present invention without departing from the spirit thereof, and the invention includes all such modifications.

What we claim is:

1. A couch for reliably supporting and fixing in place a completely or partially anesthesized patient in a strain-free and compression-free manner, for instance to comminute renal calculi in a contact-less manner by means of shock waves, comprising four individually adjustable rests and support surfaces respectively for the two arms, the head and the shoulder of a person, the supports for the two arms being situated next to and to the side of the support for the head, above the support for the shoulder;

two separate pairs of rests and supports for the legs of the person being spaced from the said four support surfaces for establishing an unsupported area for the back of the person down from his or her shoulder to the thighs;

said two separate pairs of rests and supports each being tiltable on longitudinal parallel axes, and the rests and supports of each pair being inclinable in relation to each other.

2. A couch for patients according to claim 1 including:

a support beam (1) supported at the center thereof in an articulation (3) so as to be pivotal about an axis (4) and lockable in place and terminating in first and second hinges (5,6) each assuming two positions offset by 180 degrees, the shoulder rest and support (11) surface being pivotal about an axis (10) in an articulation (9) and lockable in place, and being secured to said first hinge (5) by an essentially U-shaped support post (8), said post (8) being pivotal about an axis (7), guides (12) at the underside of the rest and shoulder support surface (11) on both sides of the axis of rotation (10) to insert and lock in place in each case said head rest and support surface (13) and the two arm rests and support surfaces (14), the two arm rests and support surfaces (14) being so arranged that the lower arms lie next to the head, a cross-bar (17), having two parallel guides (18) extending in the longitudinal direction of the couch, mounted by means of a second, essentially L-shaped support post (16) pivotal about an axis (15) in the second hinge (6)

a foot portion resting on two rails (19) mounted in a longitudinally displaceable manner in the guides (18) of the cross-bar (17) and including four pan supports (22) pivotal by means of four articulations (21) about an axis (23);

spindles (24) being arranged cross-wise between the pan supports (22) and two cross-beams (20) secured to the rail ends the inclination of said pan supports being adjustable by changing the lengths of the spindles (24); and the supports of the two pairs of supports and rests being respectively mounted to said support pan (22).

3. A couch for patients according to claim 2 including means whereby each pan in a pair of supports can be tipped by a given amount in both directions about an axis (28) parallel to the longitudinal axis of said thigh pan or lower leg pan and can be locked into its neutral position.

4. A couch for patients according to claim 2 including straps (29, 32, 33), for securing a particular extremity, at the arm and leg rests (14, 25, 26) defining the respective rest and support surface, and a strap system (30, 31) for securing the upper body and the trunk between the rests and support surfaces for the thighs (25) and the shoulder (11).

5. A couch for patients according to claim 2 including padding on the rest and support surfaces (11, 13, 14, 25, 26) of a water-tight, closed-pore foam.

6. A couch for patients according to claim 2, in which the support beam (1), and hence its center point of support thereof, is offset from the axis of symmetry of the couch.

* * * * *